(12) United States Patent
Mazzola et al.

(10) Patent No.: US 9,150,590 B2
(45) Date of Patent: Oct. 6, 2015

(54) PROCESS FOR THE SYNTHESIS OF RIFAXIMIN AND A NEW PSEUDO-CRYSTALLINE FORM OF RIFAXIMIN OBTAINED THEREBY

(75) Inventors: Disma Mazzola, Lugano (IT); Silvia Moiana, Cantu-Como (IT); Germano Coppi, San Martino Siccomario (IT)

(73) Assignee: Friulchem Spa (IT)

( * ) Notice: Subject to any disclaimer, the term of this patent is extended or adjusted under 35 U.S.C. 154(b) by 0 days.

(21) Appl. No.: 14/118,561

(22) PCT Filed: May 21, 2012

(86) PCT No.: PCT/EP2012/059404
§ 371 (c)(1),
(2), (4) Date: Feb. 7, 2014

(87) PCT Pub. No.: WO2012/156533
PCT Pub. Date: Nov. 22, 2012

(65) Prior Publication Data
US 2014/0155422 A1    Jun. 5, 2014

(30) Foreign Application Priority Data

May 19, 2011   (WO) .................. PCT/EP2011/058171

(51) Int. Cl.
*A61K 31/44*   (2006.01)
*C07D 498/22*   (2006.01)

(52) U.S. Cl.
CPC .................................... *C07D 498/22* (2013.01)

(58) Field of Classification Search
None
See application file for complete search history.

(56) References Cited

U.S. PATENT DOCUMENTS

2009/0082558 A1    3/2009   Kothakonda et al.

FOREIGN PATENT DOCUMENTS

| CN | 101585843 A | 11/2009 |
|---|---|---|
| EP | 0161534 A2 | 11/1985 |
| EP | 1557421 A1 | 7/2005 |
| EP | 1676848 A1 | 7/2006 |
| WO | 2005/044823 A2 | 5/2005 |
| WO | 2008/035109 A1 | 3/2008 |
| WO | 2008/155728 A1 | 12/2008 |
| WO | 2009/108730 A2 | 9/2009 |

*Primary Examiner* — Heidi Reese
(74) *Attorney, Agent, or Firm* — Banner & Witcoff, Ltd.

(57) ABSTRACT

Process for the preparation of rifaximin, pseudo-crystalline rifaximin and a new pseudo-crystalline form of rifaximin with fewer impurities obtained thereby.

11 Claims, 5 Drawing Sheets

Peak Search

Figure 1:
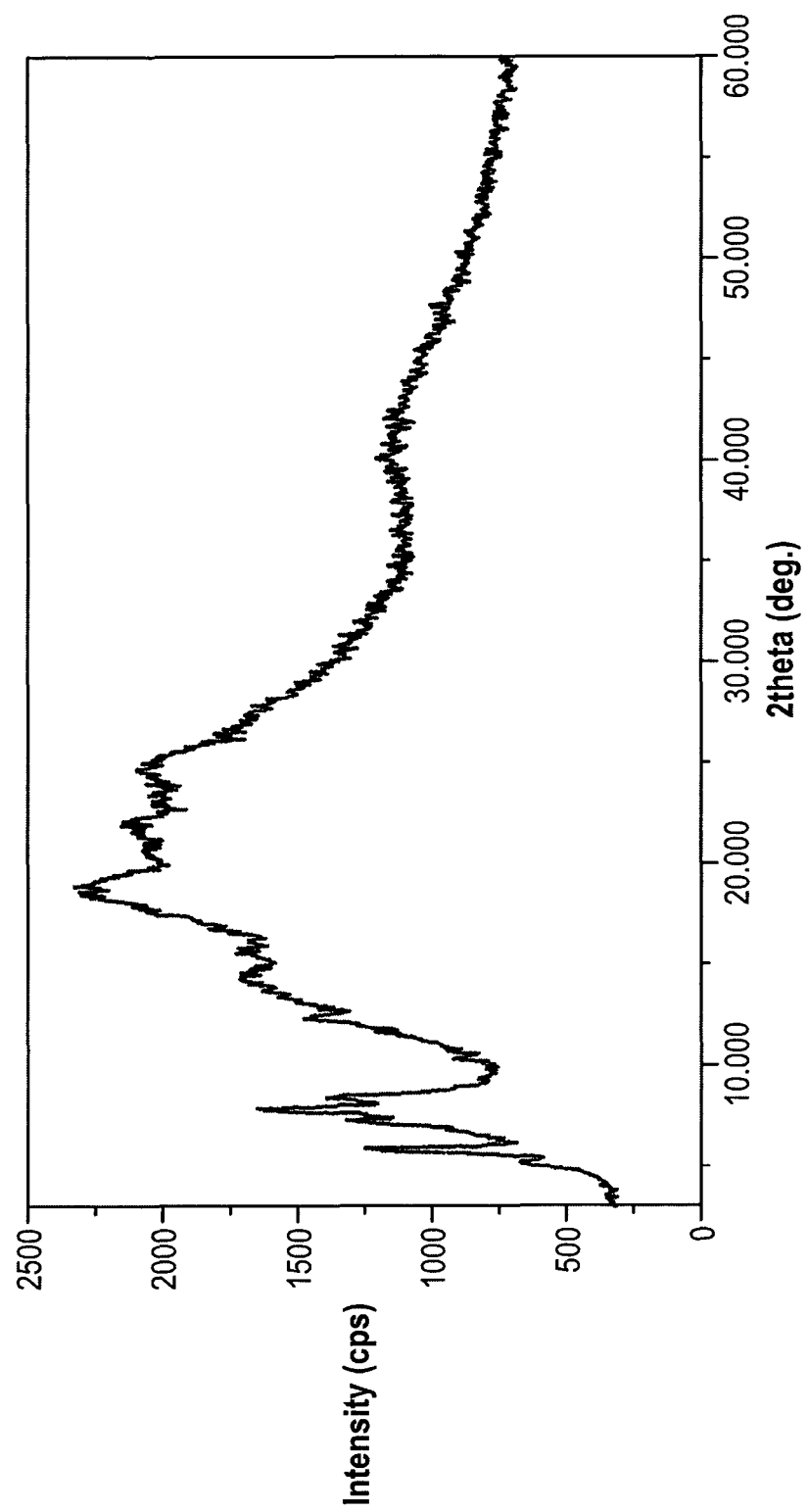

| Sample | : rifaxiRIFA-031007 | | | File | : RIF31007.RAW | | Date | : Apr-19-11 11:49:24 | | Operator | : | |
|---|---|---|---|---|---|---|---|---|---|---|---|---|
| Comment | : | | | Memo | : Normal | | | | | | | |
| method | : 2nd differential | | | Typical width | | : 0.200 deg. | | Min. height | | : 200.00 cps | | |
| Peak no. | 2theta | FWHM | d-value | Intensity | I/Io | Peak no. | 2theta | FWHM | d-value | Intensity | I/Io |
| 1 | 5.180 | 0.259 | 17.0453 | 671 | 29 | 31 | 18.460 | 0.141 | 4.8021 | 2251 | 98 |
| 2 | 5.920 | 0.329 | 14.9162 | 1253 | 55 | 32 | 19.080 | 0.118 | 4.6475 | 2316 | 100 |
| 3 | 6.280 | 0.118 | 14.0619 | 756 | 33 | 33 | 19.240 | 0.118 | 4.6092 | 2252 | 98 |
| 4 | 6.860 | 0.118 | 12.8743 | 952 | 42 | 34 | 19.800 | 0.141 | 4.4801 | 2132 | 93 |
| 5 | 7.200 | 0.118 | 12.2671 | 1204 | 52 | 35 | 20.000 | 0.118 | 4.4357 | 2065 | 90 |
| 6 | 7.300 | 0.165 | 12.0992 | 1323 | 58 | 36 | 20.520 | 0.118 | 4.3245 | 2063 | 90 |
| 7 | 7.860 | 0.400 | 11.2384 | 1655 | 72 | 37 | 20.700 | 0.118 | 4.2873 | 2067 | 90 |
| 8 | 8.460 | 0.282 | 10.4427 | 1396 | 61 | 38 | 20.800 | 0.118 | 4.2669 | 2079 | 90 |
| 9 | 9.020 | 0.141 | 9.7956 | 918 | 40 | 39 | 21.160 | 0.118 | 4.1951 | 2073 | 90 |
| 10 | 11.720 | 0.118 | 7.5443 | 1207 | 53 | 40 | 21.460 | 0.165 | 4.1371 | 2090 | 91 |
| 11 | 12.060 | 0.118 | 7.3323 | 1285 | 56 | 41 | 22.180 | 0.141 | 4.0044 | 2156 | 94 |
| 12 | 12.420 | 0.141 | 7.1206 | 1483 | 65 | 42 | 22.380 | 0.165 | 3.9691 | 2092 | 91 |
| 13 | 12.560 | 0.118 | 7.0415 | 1457 | 63 | 43 | 23.260 | 0.118 | 3.8209 | 2046 | 89 |
| 14 | 12.860 | 0.118 | 6.8779 | 1408 | 61 | 44 | 23.520 | 0.118 | 3.7792 | 2036 | 88 |
| 15 | 13.220 | 0.118 | 6.6914 | 1510 | 66 | 45 | 23.700 | 0.118 | 3.7509 | 2043 | 89 |
| 16 | 13.440 | 0.212 | 6.5824 | 1557 | 68 | 46 | 23.900 | 0.118 | 3.7200 | 2008 | 87 |
| 17 | 13.740 | 0.341 | 6.4393 | 1630 | 71 | 47 | 24.300 | 0.118 | 3.6597 | 2023 | 88 |
| 18 | 14.240 | 0.188 | 6.2143 | 1705 | 74 | 48 | 24.460 | 0.118 | 3.6361 | 2063 | 90 |
| 19 | 14.940 | 0.118 | 5.9247 | 1654 | 72 | 49 | 24.740 | 0.212 | 3.5956 | 2097 | 91 |
| 20 | 15.420 | 0.118 | 5.7414 | 1654 | 72 | 50 | 25.120 | 0.165 | 3.5420 | 2083 | 90 |
| 21 | 15.600 | 0.118 | 5.6755 | 1731 | 75 | 51 | 25.440 | 0.118 | 3.4982 | 2020 | 88 |
| 22 | 15.820 | 0.188 | 5.5971 | 1697 | 74 | 52 | 25.640 | 0.118 | 3.4714 | 1980 | 86 |
| 23 | 16.140 | 0.118 | 5.4868 | 1672 | 73 | 53 | 26.180 | 0.141 | 3.4010 | 1855 | 81 |
| 24 | 16.620 | 0.141 | 5.3294 | 1757 | 76 | 54 | 26.400 | 0.118 | 3.3731 | 1793 | 78 |
| 25 | 16.880 | 0.165 | 5.2479 | 1825 | 79 | 55 | 26.580 | 0.141 | 3.3507 | 1814 | 79 |
| 26 | 17.200 | 0.141 | 5.1510 | 1855 | 81 | 56 | 26.800 | 0.118 | 3.3237 | 1779 | 77 |
| 27 | 17.380 | 0.118 | 5.0980 | 1886 | 82 | 57 | 27.620 | 0.118 | 3.2268 | 1677 | 73 |
| 28 | 17.680 | 0.118 | 5.0122 | 2035 | 88 | 58 | 27.980 | 0.118 | 3.1861 | 1675 | 73 |
| 29 | 18.000 | 0.141 | 4.9238 | 2104 | 91 | 59 | 28.320 | 0.118 | 3.1486 | 1609 | 70 |
| 30 | 18.340 | 0.141 | 4.8333 | 2178 | 94 | 60 | 29.120 | 0.165 | 3.0639 | 1510 | 66 |

Fig. 2

PROCESS FOR THE SYNTHESIS OF RIFAXIMIN AND A NEW PSEUDO-CRYSTALLINE FORM OF RIFAXIMIN OBTAINED THEREBY

RELATED APPLICATION DATA

This application is a National Stage Application under 35 U.S.C. 371 of co-pending PCT application PCT/EP2012/059404 designating the United States and filed May 21, 2012; which claims the benefit of PCT application number PCT/EP2011/058171 and filed May 19, 2011 each of which are hereby incorporated by reference in their entireties.

The present invention is related to new methods for preparing highly purified rifaximin and to a new pseudo-crystalline form of rifaximin.

Rifaximin (The Merk Index XIII Ed., 8304) is a semi-synthetic antibiotic related to rifamycin. It has a broad spectrum of activity covering most intestinal germs and it is almost non absorbable from the gastrointestinal tract. It is therefore used as a non absorbable intestinal disinfectant.

A process for one step synthesis of rifaximin from rifamycin O (The Merk Index XIII Ed., 8301) has been described in EP 0 161 534. This document also describes crystallization and further purification of rifaximin; crystallization may be carried out in suitable solvent systems but the crystalline form which is obtained has not been further characterized. According to the examples, rifaximin may typically be crystallized from a 7:3 mixture of ethyl alcohol/water and may be dried both under atmospheric pressure and under vacuum.

EP 1 557 421, EP 1 676 848 and WO2005/044823 describe different polymorphs of rifaximin, with particular emphasis on crystalline forms α and β and a poorly crystalline γ form. The amorphous form shows increased bioavailability compared to the crystalline forms which are not absorbed.

Various amorphous or poorly crystalline forms of rifaximin have also been described in WO 2008/155728, US 2009/0082558, WO 2008/035109 and WO 2009/108730. These polymorphic forms are obtained under different experimental conditions and are characterized by their XRPD pattern.

In the methods of the prior art the polymorphic form which is obtained depends on the final water content of the rifaximin. Transition between different polymorphic forms of rifaximin occurs by drying or wetting of the synthesized rifaximin.

Moreover, the methods for synthesis and purification of rifaximin described in the state of the art lead to the presence of various impurities in rifaximin. In the European Pharmacopoeia (6.5 07/2009:2362), the monograph for rifaximin refers to various impurities identified as impurities A, B, C, D, E, F, G and H as determined by liquid chromatography. Various unspecified impurities are also present. This monograph further defines the required specifications for rifaximin with respect to some of these different impurities.

Unexpectedly, the process for preparing rifaximin according to the present invention yields a product with a very low amount of impurities. This process also yields a new pseudo-crystalline form of rifaximin. Advantageously, the new pseudo-crystalline rifaximin of the present invention displays increased stability in the presence of water and is polymorphically stable at water contents comprised between 0.5% and 7%.

SUMMARY OF THE INVENTION

The present invention is related to a process for the preparation of rifaximin comprising the following steps:

a) Reacting under stirring a molar equivalent of rifamycin O with an excess of 2-amino-4-methylpyridine in a solvent comprising water, ethyl alcohol and acetone, at a temperature comprised between 15° C.-40° C. and for a period of time comprised between 20-35 hours;
b) Precipitating the solid by cooling the solution;
c) Filtering and washing the precipitated solid;
d) Suspending the precipitated solid in a mixture of ethyl alcohol and water comprising at least 95% ethyl alcohol, under heating at a temperature comprised between 35° C.-45° C. for 2.5-3.5 hours under stirring;
e) Cooling the suspension to a temperature of 10° C. in 60 minutes and keeping the solution at 10° C. for at least 30 additional minutes;
f) Filtering and washing the resulting solid;
g) Drying the solid.

Preferably, the 2-amino-4-methylpyridine is from 2 to 4 molar equivalents. Advantageously, the solvent comprises water, ethyl alcohol and acetone in a volumetric ratio comprised between 6:3:2 and 3:3:1. More preferably, the solvent comprises water, ethyl alcohol and acetone in a volumetric ratio of 4:3:1.

Preferably, the reaction in step a) is performed at a pH comprised between 9.0 and 9.5.

Preferably, precipitating the solid in step b) is performed by cooling the solution to a temperature comprised between 0° C.-15° C. in a period of time comprised between 15-60 minutes.

Preferably, washing the precipitated solid in step c) comprises washing with a mixture of ethyl alcohol/water and final washing with water.

Preferably, in step d) the solid is suspended in ethyl alcohol and water under heating at a temperature comprised between 38° C.-42° C. for three hours.

In preferred embodiments, in step f) washing the resulting solid comprises washing with a mixture of ethyl alcohol and water.

More preferably, in step f) washing the resulting solid comprises washing with a mixture of ethyl alcohol and water in a volumetric ratio 1:2.

Preferably, in step g) the solid is dried until the water content is comprised between 0.5% and 7%.

The present invention is also related to rifaximin obtained or obtainable according to the process of the present invention.

Another object of the present invention is rifaximin having the XRPD pattern as shown in FIG. 1.

The present invention is also directed to rifaximin having an XRPD pattern with main peaks at about 5.9°, 7.3°, 7.9° and 8.4° 2-theta.

Preferably, the rifaximin according to the present invention has a water content comprised between 0.5% and 7%.

DETAILED DESCRIPTION OF THE INVENTION

The present invention is related to an improved process for the synthesis of rifaximin resulting in rifaximin having fewer impurities. The new form of rifaximin obtained by this process is stable at various water contents.

The process of the present invention comprises reacting rifamycin O with an excess of 2-amino-4-methylpyridine in a solvent comprising acetone. The presence of acetone in the solvent is crucial; it lowers the yield but provides for the synthesis of rifaximin containing a very low amount of impurities. The resulting raw rifaximin may be further purified by suspending the solid in ethanol and water under heating and precipitating rifaximin by cooling. These process steps lead to a pseudo-crystalline rifaximin having a high water content compared to the crystalline or amorphous rifaximin of the state of the art. Another object of the present invention is a process for the preparation of a pseudo-crystalline rifaximin which is polymorphically stable upon storage in various conditions.

The monograph for rifaximin in the European Pharmacopoeia (Eur. Ph. 6.5) gives detailed specifications for the impurities found in rifaximin. These impurities are determined by liquid chromatography according to the protocol described in the European Pharmacopoeia.

Specified impurities comprise the following impurities:
A: 4-methylpyridin-2-amine,
B: rifamycin B,
C: rifamycin SV,
D: rifamycin Y,
E: rifamycin S,
F: rifamycin O,
G: (2S, 16Z, 18E, 20S, 21S, 22R,23R, 24R, 25S, 26R, 27S, 28E)-5,21,23-trihydroxy-27-methoxy-2,4,11,16,20,22, 24,26-octamethyl-1,6,15-trioxo-1,2,6,7-tetrahydro-2, 7-(epoxypentadeca[1,11,13]trienonitrilo)benzofuro-[4, 5-e]pyrido[1,2-a]benzimidoazol-25-yl acetate (oxidized rifaximin),
H: (2S, 16Z, 18E, 20R, 21S, 22R, 23R, 24R, 25S, 26R, 27S, 28E)-5,6,21,23-tetrahydroxy-20-(hydroxymethyl)-27-methoxy-2,4,11,16,22,24,26-heptamethyl-1, 15-dioxo-1,2-dihydro-2,7-(epoxypentadeca[1,11,13] trienoimino)benzofuro-4,5-e]pyrido[1,2-a] benzimidazol-25-yl acetate (hydroxyrifaximin).

Some uncharacterized or unspecified impurities are also present and reported in the European Pharmacopoeia.

The methods of the present invention provide for rifaximin with fewer impurities, in preferred embodiments, the processes of the present invention provide for a pseudo-crystalline form of rifaximin with fewer impurities.

In preferred embodiments, the process of the present invention provides rifaximin with fewer A impurities as identified above more particularly pseudo-crystalline rifaximin.

Advantageously, the pseudo-crystalline rifaximin is stable at a water content comprised between 0.5% and 7%. In contrast to the rifaximin of the state of the art, transition from one polymorphic form to another is not observed when the water content varies between 0.5% and 7%. Drying or wetting of the pseudo-crystalline rifaximin of the present invention does not lead to transition to another polymorphic form. Water content is typically assessed according to the Karl Fisher method.

Advantageously, the processes of the present invention are simplified in comparison with known processes for synthesizing rifaximin which involve the use of ascorbic acid and/or concentrated HCl. In the prior art, ascorbic acid is generally utilized in order to avoid the presence of the quinone form of rifaximin and to keep it in the idroquinone form. In the process of the present invention, rifaximin oxidation has never been observed and if it occurs, oxidation affects a very low percentage of the rifaximin. Concentrate HCl is commonly used to reduce the pH at values comprised between 2-3 in order to obtain a methylaminopyridine salt. The water solubility of the resulting salt permits elimination of the excess of starting material. It has now been observed that the free amine is soluble in water and it is not necessary to add HCl in order to eliminate more easily the excess methylaminopyridine.

In the processes of the present invention, the absence of salts (methylaminopyridine hydrochloride and ascorbic acid salts) and the final pH of the solution yield a pseudo-crystalline form of rifaximin which is stable at various water contents comprised between 0.5% and 7%. This pseudo-crystalline form is stable upon drying or wetting with water and transition between different polymorphic forms depending on the water content is not observed. The rifaximin obtained by the process of the present invention is polymorphically stable.

In the methods of the present invention, the synthesis of rifaximin is typically carried out at a neutral or basic pH, preferably the pH is comprised between 7-7.5, more preferably the pH is comprised between 9.0 and 9.5.

The pseudo-crystalline rifaximin of the present invention also has a different solubility compared to the rifaximin of the state of the art.

A first object of the present invention is a process for the preparation of rifaximin comprising the following steps:
a) Reacting a molar equivalent of rifamycin O with an excess of 2-amino-4-methylpyridine in a solvent comprising water, ethyl alcohol and acetone, at a temperature comprised between 15° C.-40° C. and for a period of time comprised between 20-36 hours;
b) Precipitating the solid by cooling the solution;
c) Filtering and washing the precipitated solid;
d) Drying the solid.

In another embodiment, the present invention is directed to a process for the preparation of rifaximin comprising the following steps:
a) Reacting under stirring a molar equivalent of rifamycin O with an excess of 2-amino-4-methylpyridine in a solvent comprising water, ethyl alcohol and acetone, at a temperature comprised between 15° C.-40° C. and for a period of time comprised between 20-36 hours;
b) Precipitating the solid by cooling the solution;
c) Filtering and washing the precipitated solid;
d) Suspending the solid in a mixture of ethyl alcohol and water comprising at least 95% ethyl alcohol, under heating at a temperature comprised between 35° C.-45° C. for 2.5-3.5 hours under stirring;
e) Cooling the suspension to a temperature of 10° C. in 60 minutes and keeping the solution at 10° C. for at least 30 additional minutes;
f) Filtering and washing the resulting solid;
g) Drying the solid.

Preferably, the 2-amino-4-methylpyridine is from 2.0 to 4.0 molar equivalents. Most preferably, a molar equivalent of rifamycin O is reacted with 2.5 to 3.5 molar equivalents of 2-amino-4-methylpyridine.

The solvent in which the reaction is performed comprises water, ethyl alcohol and acetone in a volumetric ratio comprised between 6:3:2 and 3:3:1. Most preferably, the solvent comprises water/ethyl alcohol/acetone in a volumetric ratio of 4:3:1. The amount of acetone used in the solvent has been selected to find a satisfying balance between high purity and good yield.

Preferably, the reaction in step a) is performed at neutral or basic pH, preferably the pH is comprised between 7-7.5, more preferably the pH is comprised between 9.0 and 9.5.

Preferably, the reaction temperature is comprised between 15°-40° C., more preferably between 20°-30° C. and even more preferably between 23°-27° C. In preferred embodiments, the reaction is performed at room temperature.

In preferred embodiments, the reaction time is comprised between 20 and 36 hours, preferably between 22-26 hours. In preferred, embodiments the reaction time is at least 24 hours.

After the reaction is completed, the solid rifaximin is precipitated according to any known technique. Typically, the solids resulting from the reaction are precipitated by cooling the solution. Precipitating the solid is for example performed by cooling the solution to a temperature comprised between 0° C.-15° C. preferably between 5° C.-10° C. in a period of time comprised between 15-60 minutes preferably between 25-40 minutes.

In preferred embodiments the solution is cooled to 10° C. in 60 minutes.

The precipitated solids are recovered by filtering and the recovered solid rifaximin is washed. Washing usually includes washing with a mixture of ethyl alcohol and water followed by further washing with water. In a first embodiment, the mixture contains ethyl alcohol and water in a volumetric ratio 1:1. In another embodiment, the mixture contains ethyl alcohol and water in a volumetric ratio 2:1. Final washing is typically carried out with water.

After washing, the rifaximin is dried according to any appropriate method. The rifaximin may be dried under vacuum or under normal pressure, in the presence of drying agents or not and at any appropriate temperature. Preferably, drying is performed under vacuum at 70° C. Typically, the rifaximin is dried until a water content between 0.5% and 7% is reached. The water content is determined by the Karl Fisher method.

At this stage, the resulting rifaximin already comprises fewer impurities than the rifaximin of the state of the art. Typically, the rifaximin comprises less than 0.5% impurities D+H. In preferred embodiments, impurities A in Rifaximine is practically absent.

In preferred embodiments, further purification of rifaximin involving suspension and precipitation of rifaximin is carried out.

Preferably, in step d) the solid is suspended in a mixture of ethyl alcohol and water comprising at least 95% ethyl alcohol per volume under heating at a temperature comprised between 35° C.-45° C., preferably between 38° C.-42° C., more preferably at 40° C. for 2.5-3.5 hours preferably for 3 hours. The mixture of ethyl alcohol and water used for suspending the rifaximin typically contains at least 95%, 96%, 97%, 97.5%, 98% or 99% of ethanol per volume. In some embodiments, rifaximin is suspended in ethyl alcohol and absolute ethyl alcohol. For example, 100 g of rifaximin are suspended in 300 ml ethyl alcohol. Preferably, 100 g of rifaximin are suspended in 150 ml of ethyl alcohol and 150 ml of absolute ethyl alcohol. This step is performed under stirring. Preferably, stirring is performed at least at 90 rpm.

In the next step, the suspension is cooled down progressively resulting in the precipitation of the rifaximin. Preferably, the suspension is cooled down progressively to 10° C. in a period of 60 minutes. Then the solution is kept under stirring at 10° C. for at least 30 additional minutes and the solid rifaximin precipitates.

In step f), washing the resulting solid preferably comprises washing with a mixture of water and ethyl alcohol. Most preferably, washing is carried out in a mixture of ethyl alcohol/water in a volumetric ratio 1:2.

In step g), the solid is preferably dried until the water content is equal or less than 7%, preferably the water content is comprised between 0.5% and 7%, more preferably between 2% and 4.5%, even more preferably between 3%-4% and most preferably the water content is about 3.5%. The rifaximin is dried according to any appropriate method. As described above, the resulting rifaximin may be dried under vacuum or under normal pressure, in the presence of drying agents or not and at any appropriate temperature. Preferably, drying is performed under vacuum at 70° C. The water content is determined by the Karl Fischer method.

The methods described above allow the synthesis of a highly purified pseudo-crystalline rifaximin which is stable at a water content comprised between 0.5% and 7% as determined by the Karl Fischer method.

The present invention is also related to a process for the preparation of pseudocrystalline rifaximin comprising the following steps:
 a) Suspending rifaximin in a mixture of ethyl alcohol and water comprising at least 95% ethyl alcohol, under heating at a temperature comprised between 35° C.-45° C. for 2.5-3.5 hours under stirring,
 b) Cooling the suspension to a temperature of 10° C. in 60 minutes and keeping the solution at 10° C. for at least 30 additional minutes,
 c) Filtering and washing the resulting solid,
 d) Drying the solid.

Preferably, in step a) the solid rifaximin is suspended in a mixture of ethyl alcohol and water comprising at least 95% ethyl alcohol under heating at a temperature comprised between 35° C.-45° C., preferably between 38° C.-42° C., more preferably at 40° C. for 2.5-3.5 hours preferably for 3 hours. The mixture of ethyl alcohol and water used for suspending the rifaximin typically contains at least 95%, 96%, 97%, 97.5%, 98% or 99% of ethanol per volume. In some embodiments, rifaximin is suspended in ethyl alcohol and absolute ethyl alcohol. For example, 100 g of rifaximin are suspended in 300 ml ethyl alcohol. Preferably, 100 g of rifaximin are suspended in 150 ml of ethyl alcohol and 150 ml of absolute ethyl alcohol. This step is performed under stirring. Preferably, stirring is performed at least at 90 rpm.

In the next step, the suspension is cooled down progressively resulting in the precipitation of the rifaximin. Preferably, the solution is cooled down progressively to 10° C. in a period of 60 minutes. Then the solution is kept under stirring at 10° C. for at least 30 additional minutes and the solid rifaximin precipitates.

In step c), washing the resulting solid preferably comprises washing with a mixture of water and ethyl alcohol. Most preferably, washing is carried out in a mixture of ethyl alcohol/water in a volumetric ratio 1:2.

In step d), the solid is preferably dried until the water content is equal or less than 7%, preferably the water content is comprised between 0.5% and 7%, more preferably between 2% and 4.5%, even more preferably between 3%-4% and most preferably the water content is about 3.5%. The rifaximin is dried according to any appropriate method. As described above, the resulting rifaximin may be dried under vacuum or under normal pressure, in the presence of drying agents or not and at any appropriate temperature. Preferably, drying is performed under vacuum at 70° C. The water content is determined by the Karl Fischer method.

The present invention is also directed to rifaximin comprising fewer impurities and in particular to rifaximin comprising less than 0.9%, 0.8%, 0.7% and more preferably less than 0.6% total impurities by weight.

In preferred embodiments, the rifaximin comprises by weight less than 0.3% impurities D and H, less than 0.1% impurity A, less than 0.1% impurity B, not more than 0.1% impurity C, less than 0.1% impurity E and less than 0.1% impurity F.

In preferred embodiments, rifaximin according to the present invention comprises less impurity A.

Impurities A, B, C, D, H, E and F are as described in the monography for rifaximin in the European Pharmacopoeia (6.5). The amount of impurities is determined by liquid chromatography applying the protocol described in the European Pharmacopoeia.

Another object of the present invention is pseudo-crystalline rifaximin having a water content equal or less than 7%, preferably the water content is comprised between 0.5% and 7%, more preferably between 2% and 4.5%, even more preferably between 3%-4% and most preferably the water content is about 3.5%.

Figure 3:
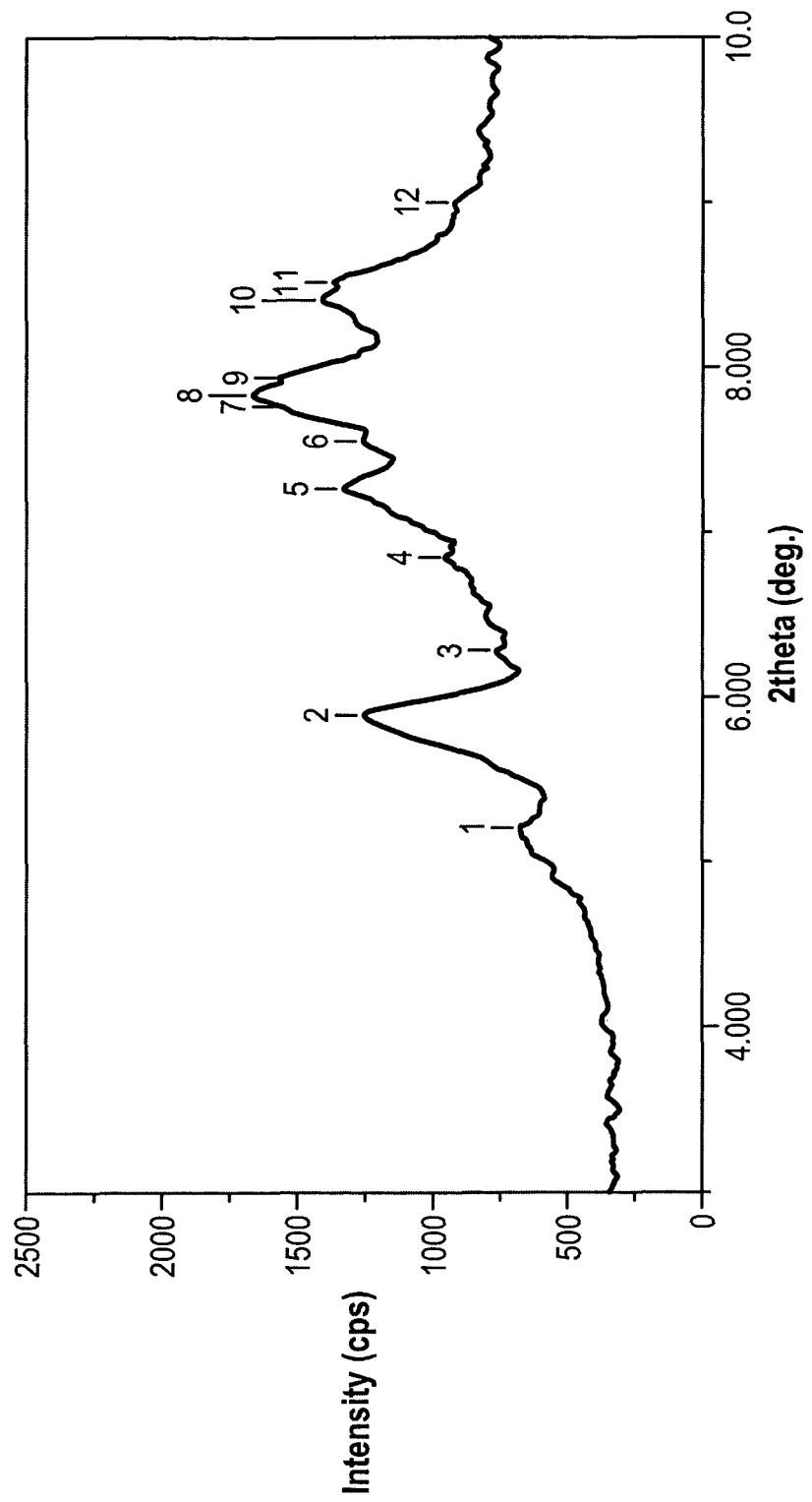

The new pseudo-crystalline rifaximin of the present invention has substantially the X-ray powder diffractogram (XRPD) pattern as shown in FIGS. 1 and 3. The XRPD pattern shows a mainly amorphous profile with some significant or main peaks characteristic of this new pseudo-crystalline form of rifaximin. Preferably, the rifaximin has an XRPD pattern with main peaks at about 5.9°, 7.3°, 7.9° and 8.4° 2-theta. More preferably, the rifaximin has an XRPD pattern with main peaks at 5.9°, 7.3°, 7.8° 7.9°, 8.0°, 8.4° and 8.6° 2-theta. Even more preferably, the rifaximin has an XRPD pattern with peaks at 5.2°, 5.9°, 6.3°, 6.9°, 7.3°, 7.6°, 7.8°, 7.9°, 8.0°, 8.4°, 8.6° and 9.0° 2-theta.

A complete list of peaks of the XRPD pattern of the rifaximin according to the present invention is shown in FIG. 2.

Advantageously, the X-ray diffractogramm of the rifaximin according to the present invention is not modified when the water content varies between 0.5% and 7%. Preferably, the bioavailability and dissolution rates are also unchanged and do not depend on the water content.

Preferably, the pseudo-crystalline rifaximin of the present invention comprises fewer impurities and in particular comprises less than 0.9%, 0.8%, 0.7% and more preferably less than 0.6% total impurities by weight.

In preferred embodiments, the pseudo-crystalline rifaximin comprises by weight less than 0.3% impurities D and H, less than 0.1% impurity A, less than 0.1% impurity B, not more than 0.1% impurity C, less than 0.1% impurity E and less than 0.1% impurity F.

The present invention is also directed to the rifaximin obtained or obtainable by the processes of the present invention.

The rifaximin according to the present invention may be advantageously used in the production of medicinal preparations having antibiotic activity, containing rifaximin, for both oral and topical use.

The present invention also encompasses pharmaceutical compositions comprising rifaximin as described herein. The present invention provides pharmaceutical compositions comprising:

a) an effective amount of rifaximin as described herein,
b) a pharmaceutically acceptable carrier.

As used herein, "pharmaceutically-acceptable carriers" includes any and all solvents, dispersion media, coatings, and the like that are physiologically compatible.

The compositions of the invention may be in a variety of forms. These include for example liquid, semi-solid, and solid dosage forms, but the preferred form depends on the intended mode of administration and therapeutic application.

These pharmaceutical compositions are preferably for oral, percutaneous and parenteral administration. In preferred embodiments, the compositions comprising rifaximin are for topical or oral administration.

The compositions as described herein may be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze. Preferred oral compositions include coated and uncoated tablets, hard and soft gelatin capsules, sugar-coated pills, lozenges, pellets, and powders.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavouring or stabilizing products.

The doses depend on the desired effect, the duration of the treatment and the route of administration used. The dosage is generally between 10 mg to 5 g, preferably 20 mg to 5 g per day per adult for intestinal infections.

In preferred embodiments, the compositions comprise rifaximin according to the present invention with carriers or excipients suitable for topical administration. Preferred compositions for topical administration of rifaximin according to the invention include ointments, pomades, creams, gels, and lotions.

In preferred embodiments, the pharmaceutical compositions for oral use contain rifaximin together with the usual excipients as diluting agents like mannitol, lactose and sorbitol; binding agents like starcks, gelatins, sugars, cellulose derivatives, natural gums and polyvinylpyrrolidone; lubricating agents like talc, stearates, hydrogenated vegetable oils, polyethylenglycol and colloidal silicon dioxide; disintegrating agents like starcks, celluloses, alginates, gums and reticulated polymers; coloring, flavoring and sweetening agents.

All the solid preparations administrable for oral route can be used in the ambit of the present invention, for instance coated and uncoated tablets, capsules made of soft and hard gelatin, sugar-coated pills, lozenges, pellets and powders in sealed packets.

The pharmaceutical compositions for topical use contain rifaximin together with the usual excipients like white petrolatum, white wax, lanolin and derivatives thereof, stearylic alcohol, propylenglycol, sodium lauryl sulfate, ethers of the fatty polyoxyethylene alcohols, sorbitan monostearate, glyceryl monostearate, propylene glycol monostearate, polyetilene glycols, methylcellulose, hydroxymethylpropylcellulose, sodium carboxymethylcellulose, colloidal aluminium and magnesium silicate, sodium alginate.

All the topical preparations can be used in the ambit of the present invention, for instance ointments, pomades, creams, gels and lotions.

The invention is hereinbelow illustrated by some examples which are not intended to limit the invention.

FIGURES

Figure 4:
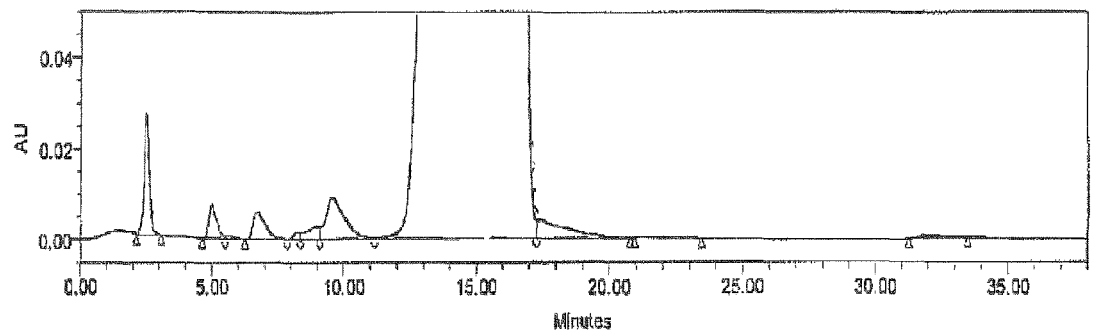
Figure 5:
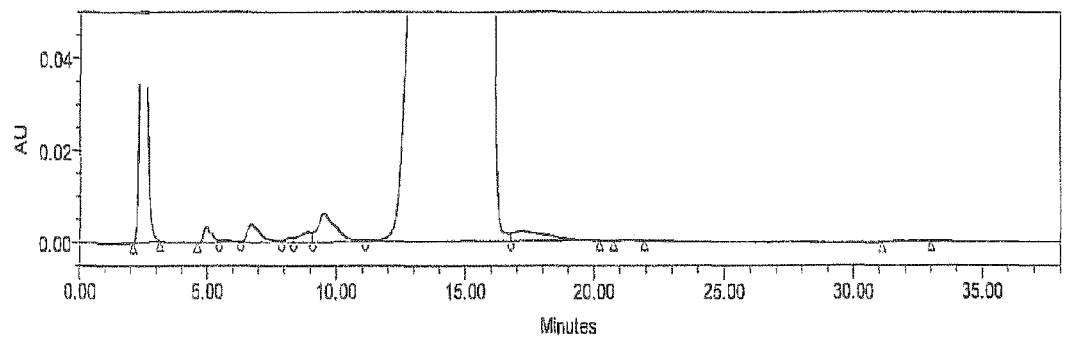

FIG. 1: XRPD pattern of rifaximin.
FIG. 2: List of XRPD peaks for rifaximin.
FIG. 3: Partial enlarged XRPD pattern of rifaximin (range 3°-10° 2θ).
FIG. 4: Chromatogram of rifaximin obtained according to example 1.
FIG. 5: Chromatogram of rifaximin obtained according to example 9 of EP 0 161 534.

EXAMPLES

Example 1

Preparation of Rifaximin

In flask equipped with a mechanic stirrer, 200 ml of demineralized water, 150 ml of ethyl alcohol, 50 ml of acetone, 100 g of Rifamycin O and 43.3 g of 2-amino-4-methylpyridine are loaded in succession at room temperature. After loading, the mixture is kept under stirring at room temperature for 24 hours, then is cooled to 10° C. for 60 minutes. Then the precipitate is filtered and washed by means of a mixture of 100 ml of demineralized water and 100 ml of ethyl alcohol and at least with two washing of 100 ml of demineralized water. The product is dried under vacuum at 70° C. until the water content is between 2.0 and 4.5%.

The dried raw Rifaximin obtained according to this process has a very low amount of impurities.

Example 2

Preparation of Highly Purified Rifaximin

To 100 g of raw Rifaximin were added 150 ml of ethyl alcohol and 150 ml of absolute ethyl alcohol. The mixture was heated at 38-42° C. for three hours and then cooled in a period of 60 minutes to 10° C. After the suspension was kept additionally 30 minutes at 10° C. and then filtered and washed with 200.00 ml of ethanol/water (1:2 v/v).

The product is dried under vacuum at 70° C. until to a Karl-Fischer water content of 3.5%. The Rifaximin is obtained with a good yield (80-85% w/w) and with a surprisingly high degree of purity compared to rifaximin as reported in the European Pharmacopoeia.

Analytical Data

The I.R. spectra have been performed in KBr with a Perkin-Elmer 281-B spectrophotometer.

The $^1$H-NMR and $^{13}$C-NMR spectra have been performed in deuterochloroform with Varian XL 100 spectrophotometer by using tetramethylsilane as internal standard.

The U.V. spectra have been performed in absolute methanol with a Perkin-Elmer 552 spectrophotometer.

The diffractograms have been carried out by using the SIEMENS D5000 instrument and under the following working conditions:

Radiation used: Kα of Copper (λ=1.5406 Å)

Tension of the generator: KV 35

Current of the generator: 30 mA

Starting and final angular 2θ value: from 2.0° to 60.0°.

The powder X-ray diffractogram of pseudocrystalline rifaximin according to the present invention is shown in FIGS. 1 and 3.

Example 3

Analytical Examination of Impurities Present in Different Rifaximins

Impurities were determined according to the liquid chromatography method described in the European Pharmacopoeia rifaximin monograph (Eur. Ph. 6.5).

In the representative Table 1, we report the specifications of rifaximin according to the European Pharmacopoeia, the impurities for rifaximin obtained according to the process of EP 0 161 543 and the impurities for the rifaximin of the present invention as obtained according to example 2.

TABLE 1

Impurities profile of different rifaximin forms

| Impurities | Eur. Ph. (6.5) Specification for Rifaximin | Rifaximin (α form) according to EP 0 161 534 (example 9) | Rifaximin according to example 2 of the present application |
|---|---|---|---|
| Impurities D + H | Not more than 0.50% | 0.36% | 0.24% |
| Impurity A | Not more than 0.10% | 2.88% | — |
| Impurity B | Not more than 0.10% | 0.17% | — |
| Impurity C | Not more than 0.10% | 0.10% | 0.10% |
| Impurity E | Not more than 0.10% | — | — |
| Impurity F | Not more than 0.10% | 0.02% | — |
| Individual unknown impurity | Not more than 0.10% | Many impurities | Only some impurities |
| Total impurities | Not more than 1.00% | 4.40% | 0.58% |

In FIGS. 4 and 5 we report chromatograms of rifaximin obtained according to example 1 of the present application (FIG. 4) and according to example 9 of EP 0 161 534 (FIG. 5). This data shows that the rifaximin obtained according to the process of the present invention contains fewer impurities. Fewer impurities are obtained although the rifaximin obtained in example 1 is not yet highly purified. Further purification is usually carried out according to example 2.

REFERENCES

EP 0 161 534
WO 2005/044823
EP 1 676 848
WO 2008/035109
US 2009/0082558
WO 2008/155728
WO 2009/108730

The invention claimed is:

1. A process for the preparation of rifaximin comprising the following steps:
    a) Reacting under stirring a molar equivalent of rifamycin O with an excess of 2-amino-4-methylpyridine in a solvent comprising water, ethyl alcohol and acetone, at a temperature within 15° C.-40° C. and for a period of time within 20-35 hours;
    b) Precipitating the solid by cooling the solution;
    c) Filtering and washing the precipitated solid;
    d) Suspending the precipitated solid in a mixture of ethyl alcohol and water comprising at least 95% ethyl alcohol, under heating at a temperature within 35° C.-45° C. for 2.5-3.5 hours under stirring;
    e) Cooling the suspension to a temperature of 10° C. in 60 minutes and keeping the solution at 10° C. for at least 30 additional minutes;
    f) Filtering and washing the resulting solid;
    g) Drying the solid.

2. The process for the preparation of rifaximin according to claim 1 wherein the 2-amino-4-methylpyridine is from 2 to 4 molar equivalents.

3. The process for preparation of rifaximin according to claim 1 wherein the solvent comprises water, ethyl alcohol and acetone in a volumetric ratio within 6:3:2 to 3:3:1.

4. The process for preparation of rifaximin according to claim 1 wherein the solvent comprises water, ethyl alcohol and acetone in a volumetric ratio of 4:3:1.

5. The process for preparation of rifaximin according to claim 1 wherein the reaction in step a) is performed at a pH within 9.0 to 9.5.

6. The process for the preparation of rifaximin according to claim 1 wherein precipitating the solid in step b) is performed by cooling the solution to a temperature within 0° C.-15° C. in a period of time within 15-60 minutes.

7. The process for the preparation of rifaximin according to claim 1 wherein washing the precipitated solid in step c) comprises washing with a mixture of ethyl alcohol/water and final washing with water.

8. The process for the preparation of rifaximin according to claim 1 wherein in step d) the solid is suspended in ethyl alcohol and water under heating at a temperature within 38° C.-42° C. for three hours.

9. The process for the preparation of rifaximin according to claim 1 wherein in step f) washing the resulting solid comprises washing with a mixture of ethyl alcohol and water.

10. The process for the preparation of rifaximin according to claim 1 wherein in step f) washing the resulting solid comprises washing with a mixture of ethyl alcohol and water in a volumetric ratio of 1:2.

11. The process for the preparation of rifaximin according to claim 1 wherein in step g) the solid is dried until the water content is within 0.5% and 7%.

\* \* \* \* \*